United States Patent [19]
Boebel

[11] Patent Number: 4,759,364
[45] Date of Patent: Jul. 26, 1988

[54] PINCERS ATTACHMENT FOR A SURGICAL HANDLE TO BE USED IN ENDOSCOPY

[75] Inventor: Manfred Boebel, Oetisheim, Fed. Rep. of Germany

[73] Assignee: Richard Wolf GmbH, Knittlingen, Fed. Rep. of Germany

[21] Appl. No.: 901,517

[22] Filed: Aug. 28, 1986

[30] Foreign Application Priority Data

Sep. 19, 1985 [DE] Fed. Rep. of Germany ....... 3533423

[51] Int. Cl.⁴ ............................................. A61B 17/12
[52] U.S. Cl. .................................... 128/326; 128/325
[58] Field of Search ................................. 128/325–326, 128/334 R, 346, 321

[56] References Cited

U.S. PATENT DOCUMENTS

| | | | |
|---|---|---|---|
| 4,064,881 | 12/1977 | Meredith | 128/325 |
| 4,169,476 | 10/1979 | Hiltebrandt | 128/325 |
| 4,394,864 | 7/1983 | Sandhans | 128/325 |
| 4,440,170 | 4/1984 | Golden et al. | 128/325 |
| 4,602,631 | 7/1986 | Funatsu | 128/325 |
| 4,635,634 | 1/1987 | Santos | 128/325 |

Primary Examiner—C. Fred Rosenbaum
Assistant Examiner—Gene B. Kartchner
Attorney, Agent, or Firm—Hill, VanSanten, Steadman & Simpson

[57] ABSTRACT

A pincers attachment for a surgical handle has a connecting rod which is axially displaceable by operation of the handle. At the distal end of a shaft there is a laterally opening recess for receiving a clip having compressible legs. The distal end of the connecting rod is connected to a closing rod which presses the legs of the clip together in the recess when the handle is actuated.

15 Claims, 1 Drawing Sheet

PINCERS ATTACHMENT FOR A SURGICAL HANDLE TO BE USED IN ENDOSCOPY

BACKGROUND OF THE INVENTION

The invention relates to a pincers attachment for a surgical handle. Pincers attachments of this kind are known, for example, from DE-GM No. 83 16 034. The known pincers attachments are employed for carrying out various surgical operations in body cavities, for example in the rectum. Different pincers attachments for performing different procedures can be coupled selectively by coupling parts to the handle which has a fixed grip leg and a grip leg which is articulated on the fixed leg.

Although it is known to stitch wounds arising during endoscopic surgical operations, there are nevertheless difficulties in ensuring that the thread ends of the suture are secured satisfactorily when they are knotted.

It is also known, when sewing wounds on the body surface, to use metal clips to secure the ends of the sewing thread. A particular thread end is inserted between two clip legs which enclose an approximately V-shaped cut-out and is secured firmly when the two clip legs are pressed together. However, it has not been possible to attach clips of this type in body cavities, particularly in the rectum, by means of known instruments of the pincers type.

A main object of the invention, is to provide a pincers attachment of the above mentioned kind which is so designed that it is possible to attach metal clips to thread ends in body cavities, especially deep in the rectum, by means of such a pincers attachment.

SUMMARY OF THE INVENTION

According to the invention there is provided a pincers attachment for a surgical handle, to be used in endoscopy, with an outer shaft and a connecting rod axially displaceable in the shaft, the shaft and connecting rod being provided at their proximal ends with coupling parts which can be fastened respectively to two relatively displaceable parts of a surgical handle, characterised in that near the distal end of the shaft there is a laterally opening recess for receiving a clip having compressible legs, and in that the distal end of the connecting rod is connected to a closing rod which is guided in a longitudinal bore in the shaft, which bore opens into the recess.

The pincers attachment merely has to be coupled to the surgical handle used for surgical operations of this type, and then a metal clip is pressed under slight prestress into the recess in the shaft firmly enough to ensure that it cannot fall out during subsequent handling and introduction into the body cavity. As soon as the thread end to be secured is inserted between the clip legs, the grip legs of the handle are squeezed together and the connecting rod and the closing rod are displaced in the shaft, so that the distal end of the closing rod presses on the adjacent leg of the clip, closes the clip and thus secures the thread end in the clip. When the spring-loaded grip legs of the handle are released, the connecting rod and the closing rod move in the proximal direction to free the clip which is still located in the recess.

To match the shape of the clip more closely, the recess widens outwardly, preferably with an approximately V-shaped cross-section.

The recess may extend transversely into the shaft over the greater part of the shaft diameter. The diameter of the shaft can then be kept relatively small.

The longitudinal bore guiding the closing rod and located in the shaft is preferably offset towards the open side of the recess relative to the central axis of the shaft. This makes it easier to close the clip legs.

In a preferred embodiment of the invention, each of the proximal and distal side faces of the recess has a substantially V-shaped depression for receiving a clip leg. This makes it easier to position and retain the clip legs in the recess.

In order to secure temporarily the clip which is inserted in to the recess and thus prevent it from falling out inadvertently before the closing rod is actuated, the closing rod or a retaining member independent of the closing rod may be loaded in the direction of the recess by a spring. Alternative automatic clamping devices of a similar kind may be used.

The distal end of the closing rod may be bevelled in the proximal direction towards the central axis of the shaft. Thus, when the closing rod is actuated, only a radially outer edge part of the closing rod first comes up against the adjacent clip leg and subjects the latter, starting from the point of engagement, to plastic deformation. The deformation which only occurs after that in the proximal direction, prevents the thread located between the clip legs from being pushed out during the further closure of the clip, since this could happen if the inner faces of the two clip-leg jaw faces, arranged approximately in the form of a V relative to one another, were to act on the surface of the thread. The bevelled closing face of the closing rod acts fully on the leg which faces it only after the clip has been closed virtually completely, the fixing of the thread in the middle clip region being assisted additionally by the generally curved jaw shape of the clip legs.

The proximal end of the closing rod and the distal end of the connecting rod may be fastened into a connecting piston which is longitudinally displaceable in a hollow portion of the shaft. The connecting piston both provides for the relative axial offset of the connecting rod and closing rod and ensures air-tight sealing between the distal end of the pincers attachment and the ambient atmosphere. Preferably, the connecting piston is sealed in an air-tight manner in a hollow portion of the shaft by means of an O-ring.

In order to limit the axial displacement distance of the closing rod and consequently the force exerted on the clip, the axial position of the shaft relative to its coupling part, by means of which it is fastened to the handle, can be adjustable. The extent of displacement of the closing rod can be limited as desired by adjusting its axial position.

This adjustability may be ensured simply by screwing the shaft to its coupling part by means of an axial threaded connection and the relative axial position of the shaft can be set by means of a screw ring having an internal thread screwed on the external thread of the threaded connection.

BRIEF DESCRIPTION OF THE DRAWINGS

An embodiment of the invention will now be described, by way of example, with reference to the accompanying drawings, in which.

DETAILED DESCRIPTION

Figure 1:
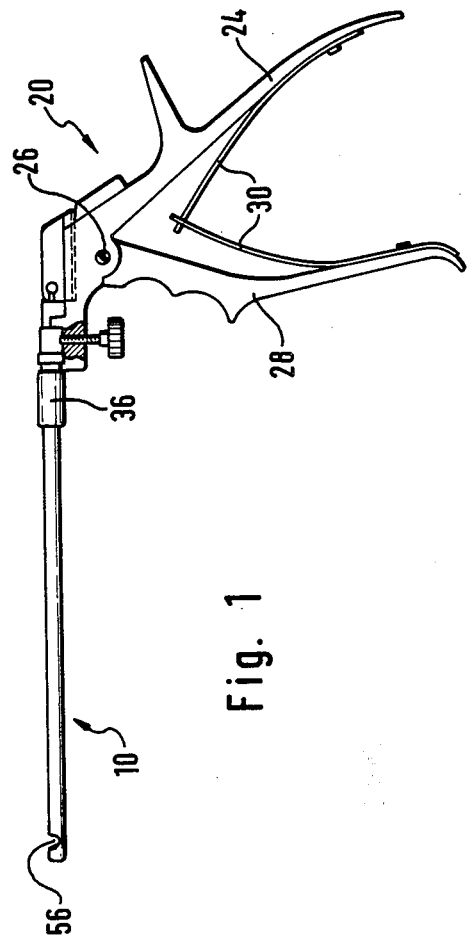
FIG. 1 is a diagrammatic elevation of a pincers attachment according to the invention, which is fastened to a surgical handle by coupling parts.
Figure 2:
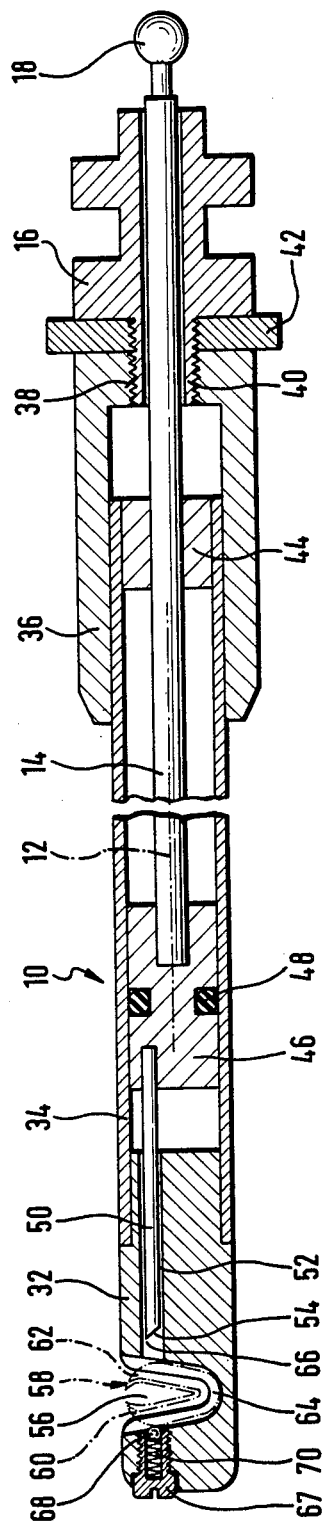
FIG. 2 shows an enlarged axial section through the pincers attachment of FIG. 1 with a clip inserted into a recess in the shaft of the attachment.

A pincers attachment has a shaft, indicated generally by 10, and a connecting rod 14 which is displaceable in the shaft along its central axis 12. The shaft 10 carries a coupling part 16 at its proximal end, and the connecting rod 14 carries a spherical coupling part 18 at its proximal end. The two coupling parts 16 and 18 are fastened in a way not shown in detail, to the handle 20 as shown in FIG. 1. The handle 20 is not part of the present invention and is therefore only described in broad outline. Details of the handle 20 are described in DE-GM No. 83 16 034.

The handle 20 has a fixed grip leg 24 and a pivotable grip leg 28 mounted on the leg 24 so as to be pivotable about the pivot pin 26. The two grip legs are respectively connected to the two coupling parts 16 and 18. The grip legs are held in their spread position, as shown in FIG. 1, by means of springs 30. When the grip legs 24 and 28 are squeezed together against the force of the springs 30, the coupling part 18 is pushed forwardly in the distal direction against the coupling part 16. The connecting rod 14 is thereby pushed forwardly in the shaft 10.

The shaft 10 consists of a distal clip-receiving part 32, a sleeve 34, fixed to the proximal end of the part 32, and a threaded part 36, fixed to the proximal end of the sleeve 34. The threaded part 36 has, at its proximal end, an internal thread 38, into which is screwed a threaded stem 40, having an external thread, of the coupling part 16. Screwed onto the threaded stem 40, between the coupling part 16 and the threaded part 36, is a screw ring 42 which has an internal thread. Rotation of the ring 42 adjusts its axial position on the threaded stem 40, and consequently the distance between the coupling part 16 and the threaded part 36 can be adjusted. By means of this adjustment, the maximum advance of the connecting rod 14, when the grip legs 24, 28 of the handle 20 are squeezed together, can be set.

A guide element 44 for the connecting rod 14 is inserted in the proximal end of the sleeve 34. Other similar guide elements of this type can be used. The distal end of the connecting rod 14 is fastened in a connecting piston 46 which is longitudinally slidably displaceable in the sleeve 34. The connecting piston 46 is sealed in the sleeve 34 by an O-ring 48. The proximal end of a closing rod 50 is also fastened in the connecting piston 46, and is guided so as to be longitudinally displaceable in a longitudinal bore 52 of the part 32. The distal front face 54 of the closing rod 50 is bevelled in the proximal direction towards the central axis 12.

Near the distal end of the receiving part 32, a recess 56 opens to one side, and extends transversely through the receiving part over most of its diameter. The recess 56 widens towards the open side, and is provided for receiving a metal clip 58, represented by broken lines, which has compressible legs 60 and 62. The distal and proximal side faces of the recess 56 are each shaped with a continuous V-shaped depression 64, into which the legs 60 and 62 of the clip 58 fit. When the clip 58 is inserted, the legs 60 and 62 are slightly pre-stressed towards one another, so that they are held in the recess 56 and particularly in the depression 64. Inserted into the distal end of the clip receiving part 32, parallel to the central axis 12 is a hollow screw 67, in which a spherical retaining member 68 is loaded towards the recess 56 by a spring 70. The retaining member 68 additionally secures the clip 58 when inserted into the recess 56. The intensity of the securing force can be adjusted by screwing the hollow screw 67 axially. As soon as a thread end to be secured is inserted between the legs 60 and 62, the handle 20 is squeezed so that the distal edge 66 of the closing rod 50 bears against the leg 62 and subjects the clip to plastic deformation, in such a way that the thread end is secured and cannot slide out. Towards the end of the deformation of the clip the end face 54 comes fully up against the leg 62 and cause the thread end to be finally secured between the suitably shaped jaw faces of the compressed legs 60 and 62. When the grip legs 24 and 28 of the handle 20 are released, the closing rod 50 is drawn back and the clip 58 is freed from the recess 56.

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

I claim:

1. A pincers attachment for surgical handle to be used in an endoscope, said attachment comprising a hollow outer shaft of a constant diameter and a connecting rod axially displaceable in the outer shaft, said shaft and connecting rod being provided at their proximal ends with coupling parts, an axial position of the shaft relative to the coupling part being adjustable, said coupling parts being fastened respectively to two relatively displaceable parts of a surgical handle, said shaft near a distal end being provided with a solid portion with a laterally opening recess for receiving clip means having compressible legs, said solid portion having a longitudinal bore opening into the recess, a closing rod being received in said longitudinal bore and being connected to the distal end of the connecting rod so that when the displaceable parts are moved, said connecting rod urges a distal end of the closing rod into engagement with a leg of a clip means disposed in said recess to compress the legs of the clip means together.

2. A pincers attachment according to claim 1, wherein the recess has means for holding the retaining clip means therein.

3. A pincers attachment according to claim 2, wherein the means for holding comprises a retaining member being provided in a second bore in the solid portion and a spring urging the retaining member to project into said recess.

4. A pincers attachment according to claim 2, wherein the means for holding comprises spring means urging the closing rod to project into the recess.

5. A pincers attachment according to claim 1, wherein the shaft is screwed to its coupling part by means of an axial threaded connection, and the relative axial position of the shaft to its coupling part can be adjusted and fixed by means of a screw ring having an internal thread screwed on to the external thread of the threaded connection.

6. A pincers attachment for a surgical handle to be used in an endoscope, said attachment comprising a hollow outer shaft of a constant diameter and a connecting rod axially displaceable in the outer shaft, said shaft and connecting rod being provided at their proximal ends with coupling parts, said coupling parts being fastened respectively to two relatively displaceable parts of a surgical handle, said shaft near a distal end being provided with a solid portion with a laterally opening recess for receiving clip means having compressible legs, said solid portion having a longitudinal bore opening into the recess, a closing rod being received in said longitudinal bore and being connected to the distal end of the connecting rod so that when the displaceable parts are moved, said connecting rod urges a distal end of the closing rod into engagement with a leg of a clip means disposed in said recess to compress the legs of the clip means together, the recess having means for holding the retaining clip means therein, the means for holding comprising a retaining member being provided in a second bore in the solid portion and a spring urging the retaining member to project into said recess.

7. A pincers attachment according to claim 6, wherein the recess widens outwardly.

8. A pincers attachment according to claim 6 wherein the recess extends transversely through the shaft over the greater part of the shaft diameter.

9. A pincers attachment according to claim 3, wherein the longitudinal bore is offset towards the open side of the recess relative to the central axis of the shaft.

10. A pincers attachment according to claim 6, wherein each of the proximal and distal side faces of the recess has a substantially V-shaped depression for receiving a clip leg.

11. A pincers attachment according to claim 6, wherein the distal end of the closing rod is bevelled in the proximal direction towards the central axis of the shaft.

12. A pincers attachment according to claim 6, which includes a connecting piston being connected to a proximal end of the closing rod and a distal end of the connecting rod to connect the closing rod to said connecting rod, said connecting piston being longitudinally displaceable in a hollow portion of said outer shaft.

13. A pincers attachment according to claim 12, which includes means for sealing the proximal end of the outer shaft from the distal end in an air-tight manner, said means for sealing comprising an O-ring on said connecting piston.

14. A pincers attachment according to claim 6, wherein the solid portion is a separate member having the same diameter as the shaft with the recess and longitudinal bore formed therein.

15. A pincers attachment according to claim 14, wherein the longitudinal bore in said separate member is offset toward the open side of the recess relative to the central axis of the shaft and the distal end of the closing rod is beveled in the proximal direction towards the central axis of the shaft.

* * * * *